United States Patent
Ackermann et al.

(10) Patent No.: US 9,265,956 B2
(45) Date of Patent: Feb. 23, 2016

(54) DEVICES AND METHODS FOR TREATING DRY EYE IN ANIMALS

(71) Applicant: Oculeve, Inc., South San Francisco, CA (US)

(72) Inventors: Douglas Michael Ackermann, San Francisco, CA (US); James Donald Loudin, Houston, TX (US)

(73) Assignee: Oculeve, Inc., South San Francisco, CA (US)

( * ) Notice: Subject to any disclaimer, the term of this patent is extended or adjusted under 35 U.S.C. 154(b) by 0 days.

(21) Appl. No.: 14/201,753

(22) Filed: Mar. 7, 2014

(65) Prior Publication Data

US 2014/0257433 A1  Sep. 11, 2014

Related U.S. Application Data

(60) Provisional application No. 61/775,363, filed on Mar. 8, 2013.

(51) Int. Cl.
| | | |
|---|---|---|
| *A61N 1/00* | (2006.01) |
| *A61N 1/372* | (2006.01) |
| *A61N 1/36* | (2006.01) |
| *A61N 1/05* | (2006.01) |

(52) U.S. Cl.
CPC ........ *A61N 1/37217* (2013.01); *A61N 1/36046* (2013.01); *A61N 1/0526* (2013.01)

(58) Field of Classification Search
CPC .............. A01K 5/0114; A61N 1/0526; A61N 1/36046; A61N 1/37217
See application file for complete search history.

(56) References Cited

U.S. PATENT DOCUMENTS

| | | |
|---|---|---|
| 4,520,825 A | 6/1985 | Thompson et al. |
| 4,628,933 A | 12/1986 | Michelson |
| 4,868,154 A | 9/1989 | Gilbard et al. |
| 5,090,422 A | 2/1992 | Dahl et al. |
| 5,099,829 A | 3/1992 | Wu |
| 5,324,316 A | 6/1994 | Schulman et al. |
| 5,345,948 A | 9/1994 | O'Donnell, Jr. |
| 5,360,438 A | 11/1994 | Fisher |

(Continued)

FOREIGN PATENT DOCUMENTS

| | | |
|---|---|---|
| EP | 1497483 A1 | 1/2005 |
| EP | 1651307 A2 | 5/2006 |

(Continued)

OTHER PUBLICATIONS

Extended European Search received for European Patent Application No. 11842076.9, mailed on Oct. 10, 2014, 5 pages.

(Continued)

*Primary Examiner* — George Manuel
(74) *Attorney, Agent, or Firm* — Morrison & Foerster LLP

(57) ABSTRACT

Described here are devices, systems, and methods for treating a condition in an animal. Generally the systems include a stimulator that is implantable in the animal and a controller system configured to transmit one or more signals to the implanted stimulator. The controller system may have a controller configured to generate the one or more signals. The controller system may include one or more collars, bridles, horse hoods, cages, animal beds, and/or food bowls. The systems may be used to treat one or more conditions such as dry eye, and may treat the conditions in an animal such as a horse, dog, or cat.

7 Claims, 10 Drawing Sheets

(56) References Cited

U.S. PATENT DOCUMENTS

| | | | |
|---|---|---|---|
| 5,545,617 A | 8/1996 | Dartt et al. | |
| 5,843,140 A | 12/1998 | Strojnik | |
| 5,948,006 A | 9/1999 | Mann | |
| 6,035,236 A | 3/2000 | Jarding et al. | |
| 6,051,017 A | 4/2000 | Loeb et al. | |
| 6,083,251 A | 7/2000 | Shindo | |
| 6,205,359 B1 | 3/2001 | Boveja | |
| 6,208,902 B1 | 3/2001 | Boveja | |
| 6,240,316 B1* | 5/2001 | Richmond et al. | 607/42 |
| 6,246,911 B1 | 6/2001 | Seligman | |
| 6,272,382 B1 | 8/2001 | Faltys et al. | |
| 6,275,737 B1 | 8/2001 | Mann | |
| 6,277,855 B1 | 8/2001 | Yerxa | |
| 6,324,429 B1 | 11/2001 | Shire et al. | |
| 6,327,504 B1 | 12/2001 | Dolgin et al. | |
| 6,366,814 B1 | 4/2002 | Boveja et al. | |
| 6,458,157 B1 | 10/2002 | Suaning | |
| 6,505,077 B1 | 1/2003 | Kast et al. | |
| 6,535,766 B1 | 3/2003 | Thompson et al. | |
| 6,539,253 B2 | 3/2003 | Thompson et al. | |
| 6,564,102 B1 | 5/2003 | Boveja | |
| 6,658,301 B2 | 12/2003 | Loeb et al. | |
| 6,662,052 B1 | 12/2003 | Sarwal et al. | |
| 6,701,189 B2 | 3/2004 | Fang et al. | |
| 6,792,314 B2 | 9/2004 | Byers et al. | |
| 6,829,508 B2 | 12/2004 | Schulman et al. | |
| 6,871,099 B1 | 3/2005 | Whitehurst et al. | |
| 6,879,859 B1 | 4/2005 | Boveja | |
| 6,885,888 B2 | 4/2005 | Rezai | |
| 6,895,279 B2 | 5/2005 | Loeb et al. | |
| 7,067,307 B2 | 6/2006 | Hochleitner et al. | |
| 7,069,084 B2 | 6/2006 | Yee | |
| 7,142,909 B2 | 11/2006 | Greenberg et al. | |
| 7,169,163 B2 | 1/2007 | Becker | |
| 7,190,998 B2 | 3/2007 | Shalev et al. | |
| 7,225,032 B2 | 5/2007 | Schmeling et al. | |
| 7,317,947 B2 | 1/2008 | Wahlstrand et al. | |
| 7,330,762 B2 | 2/2008 | Boveja et al. | |
| 7,346,398 B2 | 3/2008 | Gross et al. | |
| 7,369,897 B2 | 5/2008 | Boveja et al. | |
| 7,477,947 B2 | 1/2009 | Pines et al. | |
| 7,502,652 B2 | 3/2009 | Gaunt et al. | |
| 7,547,447 B2 | 6/2009 | Yiu et al. | |
| 7,599,737 B2 | 10/2009 | Yomtov et al. | |
| 7,636,597 B2 | 12/2009 | Gross et al. | |
| 7,650,186 B2 | 1/2010 | Hastings et al. | |
| D613,408 S | 4/2010 | Gausmann et al. | |
| D614,303 S | 4/2010 | Gausmann et al. | |
| D614,774 S | 4/2010 | Gausmann et al. | |
| 7,725,176 B2 | 5/2010 | Schuler et al. | |
| D617,443 S | 6/2010 | Grenon et al. | |
| 7,758,190 B2 | 7/2010 | Korb et al. | |
| 7,778,703 B2* | 8/2010 | Gross et al. | 607/9 |
| 7,778,711 B2 | 8/2010 | Ben-David et al. | |
| 7,792,591 B2 | 9/2010 | Rooney et al. | |
| 7,805,200 B2 | 9/2010 | Kast et al. | |
| 7,805,202 B2 | 9/2010 | Kuzma et al. | |
| 7,805,203 B2 | 9/2010 | Ben-David et al. | |
| 7,809,442 B2 | 10/2010 | Bolea et al. | |
| 7,835,794 B2 | 11/2010 | Greenberg et al. | |
| 7,846,124 B2 | 12/2010 | Becker | |
| 7,860,570 B2 | 12/2010 | Whitehurst et al. | |
| D638,128 S | 5/2011 | Prokop et al. | |
| 7,981,095 B2 | 7/2011 | Grenon et al. | |
| 8,145,322 B1 | 3/2012 | Yao et al. | |
| 8,165,680 B2 | 4/2012 | Greenberg et al. | |
| 8,204,591 B2 | 6/2012 | Ben-David et al. | |
| 8,494,641 B2 | 7/2013 | Boling et al. | |
| 8,918,181 B2 | 12/2014 | Ackermann et al. | |
| 2001/0020177 A1 | 9/2001 | Gruzdowich et al. | |
| 2002/0035358 A1 | 3/2002 | Wang | |
| 2002/0188331 A1 | 12/2002 | Fang et al. | |
| 2003/0045909 A1 | 3/2003 | Gross et al. | |
| 2003/0114899 A1 | 6/2003 | Woods et al. | |
| 2003/0120323 A1 | 6/2003 | Meadows et al. | |
| 2003/0130809 A1 | 7/2003 | Cohen et al. | |
| 2003/0192784 A1 | 10/2003 | Zhou | |
| 2003/0233134 A1 | 12/2003 | Greenberg et al. | |
| 2004/0059466 A1 | 3/2004 | Block et al. | |
| 2004/0098067 A1 | 5/2004 | Ohta et al. | |
| 2005/0004621 A1 | 1/2005 | Boveja et al. | |
| 2005/0010250 A1 | 1/2005 | Schuler et al. | |
| 2005/0197675 A1 | 9/2005 | David et al. | |
| 2005/0251061 A1 | 11/2005 | Schuler et al. | |
| 2005/0267542 A1 | 12/2005 | David et al. | |
| 2006/0004423 A1 | 1/2006 | Boveja et al. | |
| 2006/0074450 A1 | 4/2006 | Boveja et al. | |
| 2006/0095108 A1 | 5/2006 | Chowdhury et al. | |
| 2006/0100668 A1 | 5/2006 | Ben-David et al. | |
| 2006/0142822 A1 | 6/2006 | Tulgar | |
| 2006/0161225 A1 | 7/2006 | Sormann et al. | |
| 2006/0195169 A1 | 8/2006 | Gross et al. | |
| 2006/0206155 A1 | 9/2006 | Ben-David et al. | |
| 2006/0259098 A1 | 11/2006 | Erickson | |
| 2006/0271108 A1 | 11/2006 | Libbus et al. | |
| 2007/0038267 A1 | 2/2007 | Shodo et al. | |
| 2007/0060815 A1 | 3/2007 | Martin et al. | |
| 2007/0060954 A1 | 3/2007 | Cameron et al. | |
| 2007/0150034 A1 | 6/2007 | Rooney et al. | |
| 2007/0250135 A1 | 10/2007 | Bartz-Schmidt et al. | |
| 2007/0276314 A1 | 11/2007 | Becker | |
| 2007/0299462 A1 | 12/2007 | Becker | |
| 2008/0021515 A1 | 1/2008 | Horsager et al. | |
| 2008/0082131 A1 | 4/2008 | Llanos | |
| 2008/0109054 A1 | 5/2008 | Hastings et al. | |
| 2008/0132933 A1 | 6/2008 | Gerber | |
| 2008/0140141 A1 | 6/2008 | Ben-David et al. | |
| 2008/0183243 A1 | 7/2008 | Shodo | |
| 2009/0005835 A1 | 1/2009 | Greenberg et al. | |
| 2009/0024187 A1 | 1/2009 | Erickson et al. | |
| 2009/0099626 A1 | 4/2009 | De Juan, Jr. et al. | |
| 2009/0124965 A1 | 5/2009 | Greenberg et al. | |
| 2009/0157142 A1 | 6/2009 | Cauller | |
| 2009/0157145 A1 | 6/2009 | Cauller | |
| 2009/0157147 A1 | 6/2009 | Cauller et al. | |
| 2009/0204142 A1 | 8/2009 | Becker | |
| 2009/0241840 A1 | 10/2009 | Mills | |
| 2009/0264966 A1 | 10/2009 | Blum et al. | |
| 2009/0281594 A1 | 11/2009 | King et al. | |
| 2009/0281596 A1 | 11/2009 | King et al. | |
| 2009/0306738 A1 | 12/2009 | Weiss et al. | |
| 2010/0076423 A1 | 3/2010 | Muller | |
| 2010/0087896 A1 | 4/2010 | McCreery | |
| 2010/0094280 A1 | 4/2010 | Muller | |
| 2010/0139002 A1* | 6/2010 | Walker et al. | 5/636 |
| 2010/0161004 A1 | 6/2010 | Najafi et al. | |
| 2010/0168513 A1 | 7/2010 | Pless et al. | |
| 2010/0179468 A1 | 7/2010 | Becker | |
| 2010/0274313 A1 | 10/2010 | Boling et al. | |
| 2010/0280509 A1 | 11/2010 | Muller et al. | |
| 2010/0318159 A1 | 12/2010 | Aghassian et al. | |
| 2011/0021975 A1 | 1/2011 | Covello | |
| 2011/0152969 A1 | 6/2011 | Zehnder et al. | |
| 2011/0295336 A1 | 12/2011 | Sharma et al. | |
| 2012/0130398 A1 | 5/2012 | Ackermann et al. | |
| 2012/0232615 A1 | 9/2012 | Barolat et al. | |
| 2012/0330376 A1 | 12/2012 | Flynn et al. | |
| 2013/0006326 A1 | 1/2013 | Ackermann et al. | |

FOREIGN PATENT DOCUMENTS

| | | |
|---|---|---|
| EP | 1919553 A1 | 5/2008 |
| EP | 1958661 A1 | 8/2008 |
| EP | 2205193 A2 | 7/2010 |
| EP | 2205314 A1 | 7/2010 |
| JP | 2005-52461 A | 3/2005 |
| JP | 2006-515900 A | 6/2006 |
| JP | 2007-44323 A | 2/2007 |
| JP | 2007-528751 A | 10/2007 |
| JP | 2008-183248 A | 8/2008 |
| JP | 2008-541850 A | 11/2008 |
| JP | 2010-537777 A | 12/2010 |
| WO | 00/62672 A1 | 10/2000 |
| WO | 03/087433 A1 | 10/2003 |

(56) References Cited

FOREIGN PATENT DOCUMENTS

| WO | 2005/007234 A2 | 1/2005 |
|---|---|---|
| WO | 2005/060984 A1 | 7/2005 |
| WO | 2006/127366 A1 | 11/2006 |
| WO | 2008/156501 A2 | 12/2008 |
| WO | 2009/035571 A2 | 3/2009 |
| WO | 2009/070709 A1 | 6/2009 |
| WO | 2010/027743 A1 | 3/2010 |
| WO | 2011/011373 A1 | 1/2011 |
| WO | 2012/068247 A1 | 5/2012 |
| WO | 2012/139063 A2 | 10/2012 |
| WO | 2012/139063 A3 | 12/2012 |

OTHER PUBLICATIONS

Extended European Search Report received for European Patent Application No. 12768458.7, mailed on Aug. 28, 2014, 7 pages.
Non-Final Office Action received for U.S. Appl. No. 13/298,042, mailed on Oct. 2, 2013, 10 pages.
Notice of Allowance received for U.S. Appl. No. 13/298,042, mailed on Apr. 29, 2014, 5 pages.
Notice of Allowance received for U.S. Appl. No. 13/298,042, mailed on Aug. 11, 2014, 7 pages.
Notice of Allowance received for U.S. Appl. No. 13/298,042, mailed on Nov. 13, 2014, 5 pages.
Final Office Action received for U.S. Appl. No. 13/441,806, mailed on Mar. 12, 2015, 10 pages.
Non-Final Office Action received for U.S. Appl. No. 13/441,806, mailed on Dec. 18, 2013, 9 pages.
Notice of Allowance received for U.S. Appl. No. 14/561,107, mailed on Mar. 31, 2015, 7 pages.
Notice of Acceptance Received for Australian Patent Application No. 2011328900, mailed on Mar. 10, 2015, 4 pages.
Office Action received for Australian Patent Application No. 2011328900, mailed on Feb. 28, 2014, 3 pages.
Notice of Allowance received for Chinese Patent Application No. 201180064627.8, mailed on Jun. 30, 2015, 2 pages (1 page of English Translation and 1 page of Official Copy).
Office Action Received for Chinese Patent Application No. 201180064627.8, mailed on Feb. 2, 2015, 16 pages (7 pages of English translation and 9 pages of Official Copy).
Office Action Received for Chinese Patent Application No. 201180064627.8, mailed on Jun. 20, 2014, 19 pages (6 pages of English Translation and 13 pages of Official Copy).
Office Action Received for Australian Patent Application No. 2012239966, mailed on Mar. 17, 2014, 6 pages.
Office Action received for Chinese Patent Application No. 201280028006.9, mailed on Nov. 14, 2014, 14 pages (7 paages English Translation and 7 pages of Official Copy).
Elsby et al., "Lacrimal Secretion in the Cat", Br. J. Pharmac. Chemother, vol. 29, No. 1, Jan. 1967, pp. 1-7.
Lora et al., "Lacrimal Nerve Stimulation by an Neurostimulator for Tear Production", Investigative Ophthalmology & Visual Science, vol. 50, Issue 13, Apr. 2009, 1 page.
International Preliminary Report on Patentability received for PCT Patent Application No. PCT/US2011/060989, mailed on May 30, 2013, 14 pages.
International Search Report & Written Opinion received for PCT Patent Application No. PCT/US2011/060989, mailed on Feb. 23, 2012, 16 pages.
Velikay-Parel et al., "Perceptual Threshold and Neuronal Excitability as Long-Term Safety Evaluation in Retinal Implants", Meeting Abstract at the Association for Research in Vision and Ophthalmology, Inc. Annual Meeting, Available at <http://www.abstractsonline.com/Plan/ViewAbstract.aspx?sKey=00d4c2e2-2814-48d9-b49338f4761ab4ca&cKey.9d81879a-9b1d-49c2-aff4-489d9-b493>, May 3, 2011, 2 pages.
International Search Report received for PCT Patent Application No. PCT/US2012/32629, mailed on Oct. 26, 2012, 4 pages.
Written Opinion received for PCT Patent Application No. PCT/US2012/032629, mailed on Oct. 26, 2012, 8 pages.
International Search Report & Written Opinion received for PCT Patent Application No. PCT/US2014/022158, mailed on Jul. 30, 2014, 9 pages.
Roessler et al., "Implantation and Explantation of a Wireless Epiretinal Retina Implant Device: Observations During the EPIRET3 Prospective Clinical Trial", Investigative Ophthalmology & Visual Science, vol. 50, No. 6, Jun. 2009, pp. 3003-3008.
Ruskell, Gordon L., "Distribution of Pterygopalatine Ganglion Efferents to the Lacrimal Gland in Man", Experimental Eye Research, vol. 78, No. 3, Mar. 2004, 1 page.
Non Final Office Action received for U.S. Appl. No. 13/441,806, mailed on Sep. 17, 2015, 11 pages.
Non-Final Office Action received for U.S. Appl. No. 14/816,846, mailed on Sep. 11, 2015, 5 pages.
Office Action received for Japanese Patent Application No. 2013-539971, mailed on Oct. 5, 2015, 11 pages (5 pages of English Translation and 6 pages of Official Copy).
International Preliminary Report on Patentability received for PCT Application No. PCT/US2014/022158, mailed on Sep. 17, 2015, 8 pages.
Notice of Acceptance received for Australian Patent Application No. 2012239966, mailed on Nov. 12, 2015, 3 pages.

* cited by examiner

DEVICES AND METHODS FOR TREATING DRY EYE IN ANIMALS

CROSS-REFERENCE TO RELATED APPLICATIONS

This application claims priority to U.S. Provisional Application Ser. No. 61/775,363, filed on Mar. 8, 2013, and titled "DEVICES AND METHODS FOR TREATING DRY EYE IN ANIMALS," the content of which is hereby incorporated in its entirety.

FIELD

The present invention relates generally to stimulation systems and methods for treating non-human animals. The stimulation systems may be used to stimulate one or more anatomical structures for the treatment of one or more indications, such as dry eye syndrome.

BACKGROUND

Dry eye syndrome (also known as keratoconjunctivitis sicca or "KCS") affects several animals including dogs, cats, and horses. Generally, tear film in these animals includes three layers: an oily top layer, a middle aqueous layer, and a bottom mucin layer. Dry eye syndrome typically results from a decrease in aqueous tear production. A decrease in aqueous tear production may dry the cornea and surrounding tissue (such as the conjunctiva), which may cause irritation, pigmentation, and even scarring of the cornea. In extreme cases, dry eye syndrome may result in blindness of the animal. Additionally, reduced aqueous tear production may cause mixing of the oily and mucin layers, resulting in a yellow discharge. Current treatments include application of artificial tears and medication or surgical solutions such as parotid duct transposition (which redirects saliva to the eye). Artificial tears and medication may be difficult to administer to the animal and may require lifelong administration, while parotid duct transposition may result in the formation of mineral deposits on the eye. What is needed is a system for improving tear productions in animals having dry eye syndrome.

BRIEF SUMMARY

Described here are systems and devices for treating one or more conditions in an animal. In some variations, the systems described here may comprise an implantable stimulator configured for implantation in the animal and a controller system comprising a controller. The controller may be configured to transmit one or more signals to the implantable stimulator. In some variations, the controller system may further comprise a collar configured to fit around a neck of the animal. In these variations, the controller may be connected to the collar. In some variations, the controller may comprise a coil, and the coil may be positioned around the collar. In other variations, the controller system may comprise a horse bridle or horse hood. The controller may be permanently or releasably connected to the horse bridle or horse hood. In some variations, the controller may be connected to a cheek strap, a throat lash, and/or one or more blinders of a horse bridle and a horse hood. In other variations, the connector may be configured as a hand-held device.

In other variations, the controller system may further comprise a food bowl, trough, container or the like. In some variations, the controller may be permanently or releasably connected to the food bowl. In some of these variations, the controller system comprises a motion sensor, and the controller may be configured to generate the one or more signals when the motion sensor detects a threshold level of motion. In other variations, the controller system further may comprise a cage or an animal bed, wherein the controller is connected to the cage or the animal bed. In some of these variations, the controller system may comprise a pressure sensor, and the controller may be configured to generate the one or more signals when the pressure sensor detects a threshold level of pressure applied thereto. Additionally or alternatively, the controller system may comprise a motion sensor, and the controller may be configured to generate the one or more signals when the motion sensor detects a threshold level of motion. The implantable stimulator may be any suitable stimulator, such as, for example, a passive stimulator.

Also described here are methods for treating one or more conditions in an animal. In some variations, the methods may comprise implanting a stimulator in the animal to position at least one electrode adjacent a lacrimal gland or a nictitans gland of the animal, and applying a stimulation signal to the lacrimal gland or the nictitans gland. In some of these variations, the at least one electrode may be placed adjacent the lacrimal gland, the nictitans gland, or both the lacrimal gland and the nictitans gland. In some variations, the method may further comprise transmitting at least one signal from a controller of a controller system to the stimulator. The at least one signal may be a data and/or a power signal. In some variations, the controller system may comprise a motion sensor, and the at least one signal may be transmitted when the motion sensor detects a threshold level of motion. Additionally or alternatively, the controller may comprise a pressure sensor, and the at least one signal may be transmitted when the pressure sensor detects a threshold pressure level. The controller system may further comprise a collar, bridle, or horse hood. Additionally or alternatively, the controller system may comprise a cage, animal bed, and/or a food bowl. The methods described here may be used to treat any suitable animal, such as a horse, dog, or cat.

DETAILED DESCRIPTION

Figure 1:
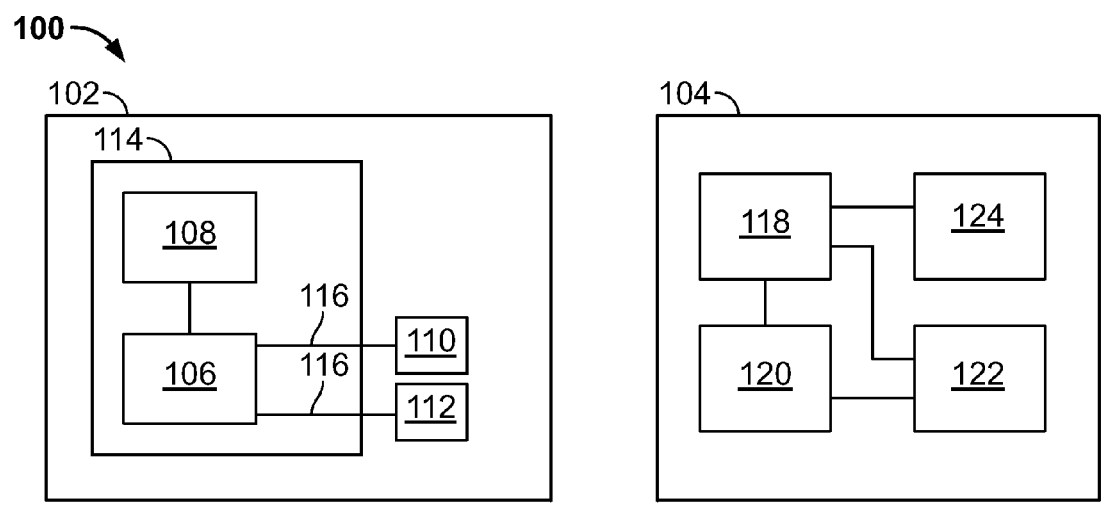
FIG. 1 depicts a block diagram of an illustrative variation of the systems described here.

Described here are stimulation systems for delivering stimulation to an animal (i.e., non-human) patient. Also described here are methods for treating one or more conditions in an animal (i.e., non-human) patient. In some variations, the stimulation systems described here may be configured to treat dry eye in an animal patient, and the methods may comprise delivering stimulation to the animal patient to treat dry eye. The systems and methods described may be used to treat any suitable non-human animal, which in some instances may be a mammal. In some variations, the systems and methods may be used to treat a horse, a cat, or a dog. Additionally, while the systems and methods described here focus on the treatment of dry eye, the stimulation systems may be used to treat any suitable condition affecting the animal patient (e.g., one or more movement disorders, endocrine disorders, bladder disorders, pain disorders, dry mouth, or the like).

Generally, the stimulation systems described here comprise at least one implantable stimulator and at least one external controller. The stimulator may be configured to deliver one or more stimulation signals to one or more target tissues of an animal when the stimulator is at least partially implanted in the animal. The stimulation provided by the stimulator may include electrical signals (e.g., one or more biphasic pulses), optical signals, acoustic signals, thermal therapy, combinations thereof and the like. In some variations, the stimulator may further be configured to release one or more drugs therefrom. Additionally or alternatively, the stimulator may be configured to monitor one or more parameters of the animal or its target tissue. For example, in some variations the stimulator may be configured to monitor neural activity in a target tissue such as the lacrimal gland, may be configured to monitor a temperature of the animal, or the like.

The external controller may be configured to transmit one or more signals to the stimulator. In some variations, the external controller may be configured to transmit a power signal to the stimulator, which may charge a power supply of the stimulator and/or power one or more portions of the stimulator. Additionally or alternatively, the external controller may be configured to transmit a data signal to the stimulator. The data signal may prompt the stimulator to take one or more actions. For example, in some variations the data signal may be used to program or reprogram the stimulator. In other instances, the data signal may instruct the stimulator to provide a particular stimulation signal to the animal, perform one or more stimulator diagnostics, or the like. In variations where the external controller is configured to transmit both power and data to the stimulator, the power and data may be transmitted via the same signal. Additionally, in some variations the stimulator may be configured to transmit data to the controller (such as stimulation logs, data relating to physical parameters monitored by the stimulator, or the like).

When the controller is configured to generate one or more signals, the one or more signals may be generated continuously or intermittently. In some instances, the controller may be configured to generate one or more signals on a planned basis. For example, the controller may be configured to generate one or more signals for certain durations at predetermined times. When the controller is configured to generate one or more signals based on measurements one or more sensors, as will be described in more detail below, the controller may generate the one or more signals when a measurement reaches a threshold level (e.g., a threshold level of motion and/or pressure). In some variations, the controller may be configured to generate the one or more signals either continuously or intermittently for as long as the threshold level is met. In other variations, the controller may be configured to generate one or more signals at one or more predetermined intervals each time the threshold level is met.

FIG. 1 shows a block diagram of a variation of a stimulation system (100) as described here. As shown there, stimulation system (100) may comprise an implantable stimulator (102) and an external controller (104). The stimulator (102) may comprise a stimulation subsystem (106) and a communication subsystem (108). The stimulation subsystem (106) may be configured to generate one or more stimulation signals which may be delivered to the animal. The communication subsystem (108) may be configured to receive one or more signals (e.g., a power and/or data signal from the external controller (104) and communicate those signals to one or more portions of the stimulator (e.g., the communication subsystem (108)). In some variations, the communication subsystem (108) may be configured to transmit one or more signals to the external controller (104). The stimulator (102) generally comprises a housing (114) that encloses some or all of the components of the stimulator (102). While the communication subsystem (108) is shown in FIG. 1 as being enclosed in the housing (114), it should be appreciated that in some instances one or more portions of the communication subsystem (108) may be positioned in the housing (114) while one or more portions of the communication subsystem (108) may be positioned externally of the housing (114).

As mentioned above, the stimulation subsystem (106) may be configured to generate one or more stimulation signals. For example, the stimulation subsystem (106) may be configured to generate an electrical stimulation signal, an optical stimulation signal, thermal signal, combinations thereof and the like. When the stimulation subsystem (106) is configured to generate an electrical stimulation signal, the electrical stimulation signal may be delivered to tissue via one or more electrodes. For example, in the variation of the stimulator (102) shown in FIG. 1, the stimulator (102) may comprise first and second electrodes (labeled (110) and (112) respectively). While the stimulator (104) is shown in FIG. 1 as comprising two electrodes, when the stimulator (104) comprises electrodes it may comprise any suitable number of electrodes (e.g., one, two, three, or four or more electrodes). Each electrode may be connected directly to the housing (114) or may be connected to the housing (114) via one or more leads (116). In some variations, a portion of the housing (114) may form an electrode.

In some variations, the stimulator (102) may be configured to detect one or more physiological parameters of the animal or of the stimulator (102). The stimulator (102) may comprise a detection subsystem (not shown) configured to monitor one or more parameters. For example, in variations where the stimulator (102) comprises one or more electrodes (such as electrodes (110) and (112)), one or more of the electrodes may be configured to detect neural activity of the animal. It should be appreciated that in these variations, each electrode may be used for detection and/or stimulation. For example, an electrode may be used for detection at a first point in time and may be used for stimulation at a second point in time.

The stimulator (102) may or may not be programmable. For example, in some variations, the stimulator (102) may be a passive stimulator. In these variations, the stimulator (102) does not include any internal logic or intelligence (e.g., ASICs, microcontrollers, or the like). In these variations, the stimulator (102) may be configured to receive power via the communication subsystem (108) (the power may be transmitted as a power signal from the controller (104)), and the stimulation subsystem (106) may be a passive dissipation circuit configured to dissipate the power received by the communication subsystem (108). The passive stimulator may be any of those described in U.S. patent application Ser. No. 13/441,806, titled "STIMULATION DEVICES AND METHODS" and filed on Apr. 6, 2012, which is hereby incorporated by reference in its entirety. Because the dissipation circuit does not include any internal logic or intelligence, the stimulation subsystem (106) may provide stimulation as long as power is supplied to the stimulation subsystem (106) and may stop providing stimulation when the power provided by the power signal is drained. In these instances, it may be necessary to occasionally provide power to the stimulator (102).

In variations where the stimulator (102) is programmable, the stimulator may comprise a processor (not shown) configured to control operation of various subsystems of the stimulator. For example, the processor may be configured to control the stimulation subsystem (106) to control the parameters of the stimulation signal generated by the stimulation subsystem (106) and/or the timing of delivery of the stimulation. The stimulator (102) may also include a memory subunit (not shown) that may be configured to store programming instructions for the stimulator (102). The programming instructions may be used to control the operation of the processor. When the stimulator is configured to monitor one or more physiological parameters of the animals or parameters of the device, information regarding these parameters may be stored in the memory subunit for later retrieval.

The stimulator (102) may or may not comprise a power supply (not shown). In variations where the stimulator (102) does comprise a power supply, the stimulator (102) may comprise any suitable power supply, such as one or more batteries. In some variations, the stimulator (102) may comprise a rechargeable power source, such as one or more rechargeable batteries. In these variations, the stimulator (102) may be configured to receive a power signal from the external controller (104) (e.g., via the communication subsystem (108)) and recharge the power source using the power signal. In other variations, the stimulator (102) may not comprise a power supply. In these variations, the stimulator may be powered by a power signal received from the external controller (104). In these variations, stimulation may be controlled by the presence or absence of a stimulation signal provided by the external controller (104) to the stimulator (102).

The communication subsystem (108) may be configured to receive any suitable type of signal provided by the external controller (104). For example, the communication subsystem (108) may be configured to receive magnetic signals, ultrasound signals, optical signals, RF signals, combinations thereof and the like. For example, in some variations the communication subsystem (108) may comprise one or more coils which may receive a signal via inductive coupling. For example, in some variations the stimulator may comprise one or more ultrasound transducers which may generate current in response to a transmitted ultrasound signal. In some variations, the ultrasound signal may be focused on the stimulator using one or more ultrasound transmitters. In other variations, the stimulator may be configured to receive optical energy (e.g., infrared, ultraviolet, visible wavelengths, or the like) and generate a current in response thereto. For example, in some variations a stimulation circuit may comprise one or more photo-voltaic elements that generate a current in response to received optical energy. In other variations, the stimulator may be configured to receive far-field RF energy. For example, high-frequency RF energy may be received by the stimulator using an antenna, and may allow for tolerance for a variety of stimulator orientations.

Figure 2A:
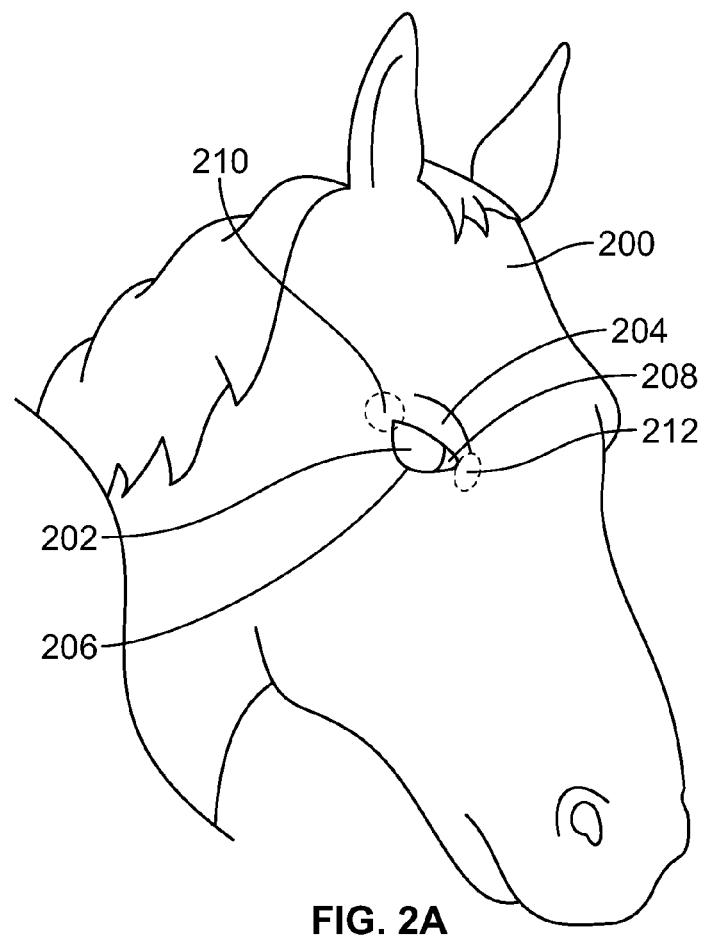
FIGS. 2A and 2B depict perspective views of the anatomy of the head of a horse and a dog, respectively.
Figure 2B:
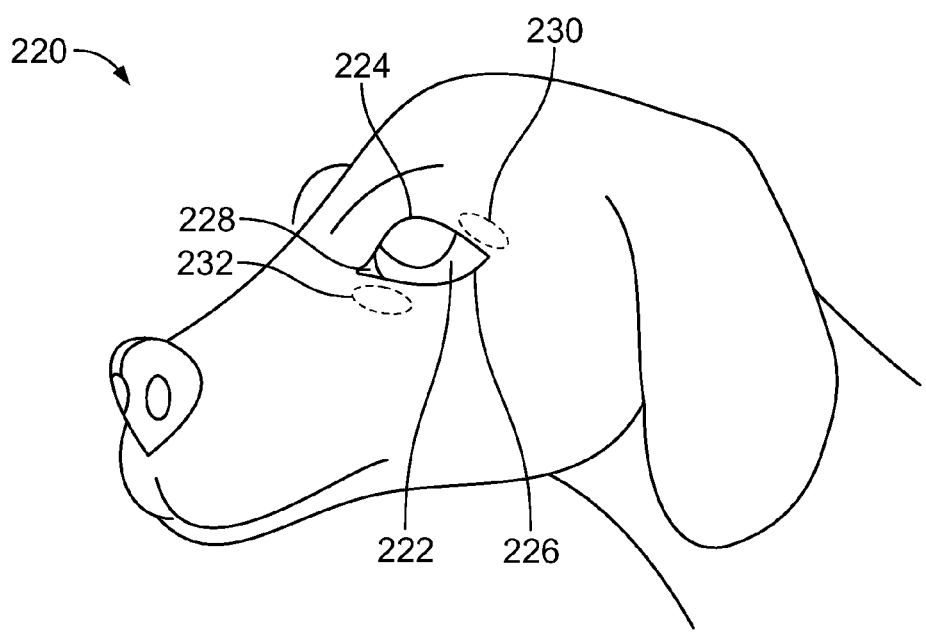

When the stimulators described here are used to treat dry eye, the stimulator may be implanted such that the stimulator may be configured to stimulate one or more nerves, tissues, glands, or other structures involved in the process of lacrimation or glandular vasodilation. For the purposes of illustration, FIGS. 2A and 2B show perspective views of the ocular anatomy of the heads of a horse and a dog, respectively. Shown in FIG. 2A is a horse (200) having an eye (202) having an upper lid (204), a lower lid (206), and a third lid (208) (also known as the nictitating membrane). Also shown there is lacrimal gland (210), which is positioned between the eye (202) and a frontal bone (not shown) of the skull. The third lid (208) also has an associated nictitans gland (212) (also known as the accessory lacrimal gland), which is positioned around cartilage (not shown) that supports the third lid (208). The lacrimal gland (210) and the nictitans gland (212) may contribute to tear formation. Similar to FIG. 2A, FIG. 2B shows a dog (220) having an eye (222) having an upper lid (224), a lower lid (226), and a third lid (228). Also shown there is a lacrimal gland (230) positioned between the eye (222) and the frontal bone (not shown) of the skull and a nictitans gland (232) positioned near third lid (228). Cats also have similarly-positioned lacrimal and nictitans glands as dogs, although the anatomy of a cat is not specifically illustrated here.

In some variations, the stimulation systems described here may be configured to stimulate the lacrimal gland. In other variations, the stimulation systems may be configured to stimulate the nictitans gland. In some variations, the stimulation systems may be configured to stimulate both the lacrimal and nictitans glands. When stimulating the lacrimal and/or nictitans gland, the stimulator of the stimulation system may stimulate one or more cells of the gland (e.g., myoepithelial cells, acinar cells, or ductal cells), one or more nerves innervating the glands (e.g., the lacrimal nerve, rami lacrimales, one or more sympathetic nerves, fibers, or neurites, one or more parasympathetic nerves, fibers, or neurites), one or more nerves of the lacrimal artery or branches thereof, combinations thereof, and the like. Other suitable stimulation targets include the meibomian/tarsal glands and/or the lacrimal ducts.

Figure 3A:
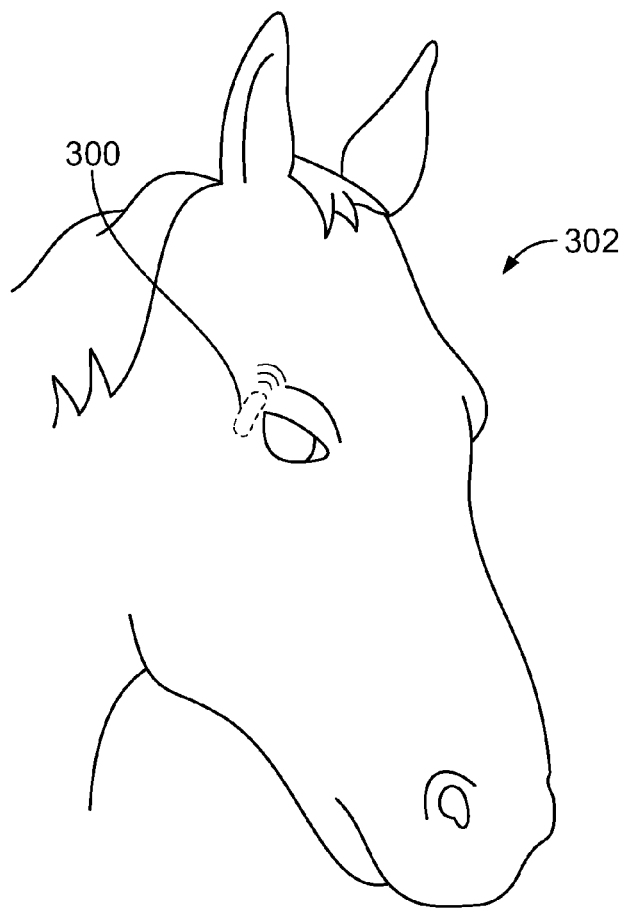
FIGS. 3A and 3B depict stimulators positioned in the anatomy of a horse and a dog, respectively.
Figure 3B:
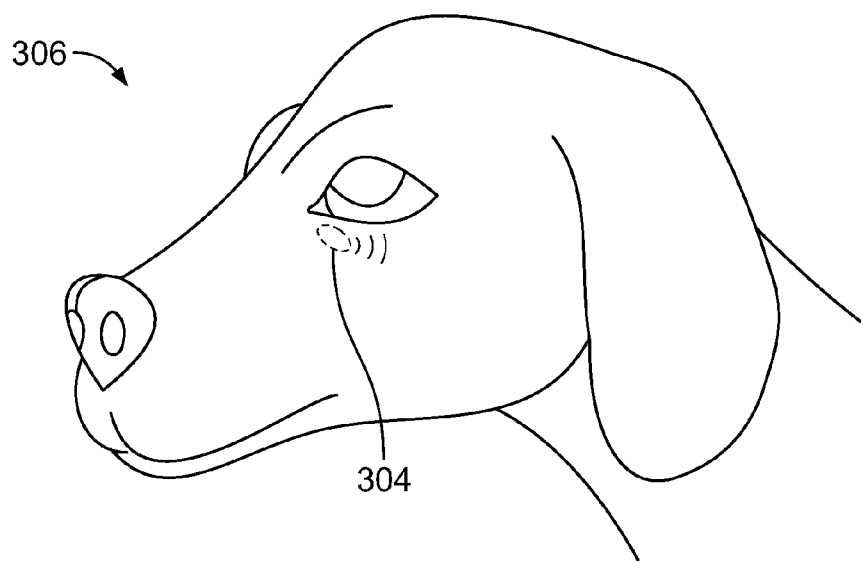

Generally, the stimulator may be positioned to place one or more electrodes adjacent to one or more of the target tissues mentioned above. In some variations, the stimulator is sized and configured to permit placement of the entire stimulator adjacent to the target tissue. For example, FIG. 3A shows a stimulator (300) positioned adjacent to the lacrimal gland (not shown) of a horse (302), and FIG. 3B shows a stimulator (304) positioned adjacent to the nictitans gland (not shown) of a dog (306). When the entire stimulator is positioned adjacent to the lacrimal gland or the nictitans gland, the stimulator may be adjacent to and directly contacting the gland, may be partially implanted within the gland, or may be fully implanted within the gland. When the stimulation system is configured to stimulate both the lacrimal gland and the nictitans gland, a first stimulator may be positioned adjacent to the lacrimal gland and a second stimulator may be positioned adjacent to the nictitans gland.

Figure 4A:
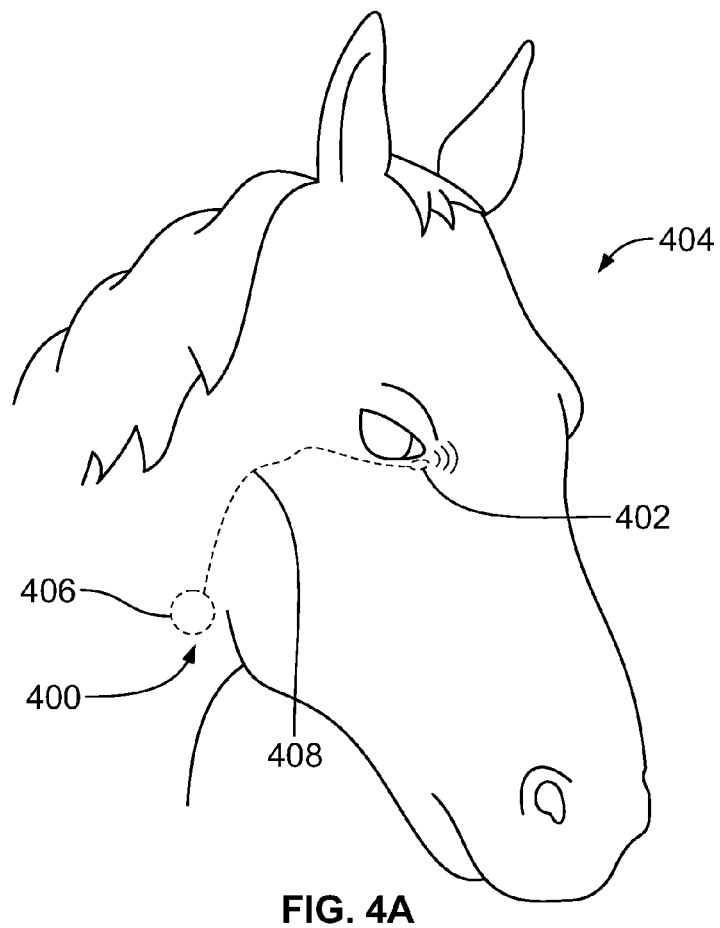
FIGS. 4A and 4B depict stimulators positioned in the anatomy of a horse and a dog, respectively.
Figure 4B:
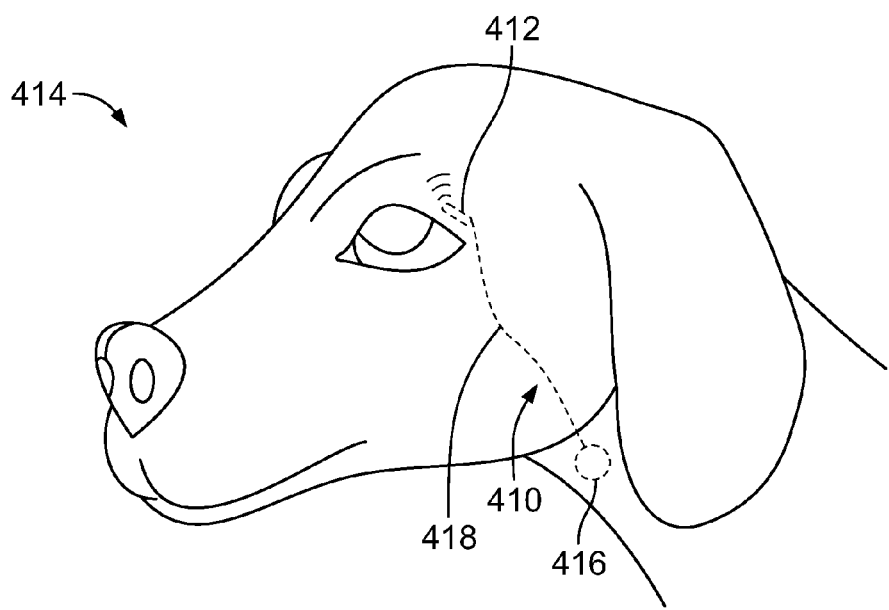

In other variations, the stimulator may be configured to position one or more electrodes of the stimulator adjacent to a target tissue and the remainder of the stimulator may be positioned remotely from the target tissue (e.g., at a position in the head, neck, or shoulders of the animal). For example, an electrode or electrodes of the stimulator may be positioned adjacent to a target tissue, and a housing of the stimulator may be positioned remotely from the target tissue with one or more leads connecting the stimulator housing to the electrode or electrodes. FIG. 4A shows a variation of a stimulator (400) comprising at least one electrode (402) positioned adjacent to the nictitans gland (not shown) of a horse (404). The stimulator (400) may also include a housing (406) which may be positioned remotely from the nictitans gland (shown in FIG. 4A as positioned in the neck of the horse (404)), and one or more leads (408) which may connect the electrode (402) to the housing (406). Positioning the housing (406) remotely from the nictitans gland may position one or more components of the stimulator (400) (e.g., a communication subsystem) remotely from the nictitans gland, which may facilitate communication between the stimulator and a controller, as described in more detail below. Similarly, FIG. 4B shows a stimulator (410) comprising at least one electrode (412) positioned adjacent to the lacrimal gland (not shown) of a dog (414). As with the stimulator (400) of FIG. 4A, the stimulator (410) may further comprise a housing (416) and one or more leads (418) connecting the at least one electrode (412) to the housing (416), which may allow the housing (416) (and any components housed therein) to be positioned remotely from the lacrimal gland (e.g., in the neck of the dog (414) as shown in FIG. 4B). When the at least one electrode is positioned adjacent to the lacrimal gland or the nictitans gland, the electrode or electrodes may be adjacent to and directly contacting the gland, may be partially implanted within the gland, or may be fully implanted within the gland. In some variations when the stimulation system is configured to stimulate both the lacrimal gland and the nictitans gland, the stimulator may comprise a first electrode or set of electrodes positioned adjacent the lacrimal gland and a second electrode or set of electrodes positioned adjacent the nictitans gland.

Returning to FIG. 1, the controller (104) of the stimulation systems described here are generally configured to transmit power and/or information to the stimulator (102). In some instances, the controller (104) may be disposable, reusable, or partially reusable. For example, in some variations one or more components of the controller may be disposable (e.g., a portion of a power supply such as a battery) may be disposable and other components (e.g., controller circuitry) may be reusable. Examples of illustrative controllers are described in U.S. patent application Ser. No. 13/441,806, filed on Apr. 6, 2012, which was previously incorporated by reference in its entirety.

Generally, the controller (104) comprises a controller subsystem (118), a communication subsystem (120), and a power supply (122). The controller subsystem (118) may be configured to generate one or more signals (e.g., one or more power and/or data signals as discussed above) and supply the signals to the communication subsystem (120). The communication subsystem (120) in turn may transmit the power and/or data signals to the communication subsystem (108) of the stimulator (102). The communication subsystem may comprise one or more coils, ultrasound generators, light sources, or the like which may transmit the output signal. For example, in some variations the communication subsystem (120) may comprise a tuning capacitor in series with a coil, which may be tuned to transmit signals at a specific frequency (e.g., 1 Mhz, or the like).

The signal transmitted by the controller (102) may be any combination of power and information. For example, in some instances the controller may be configured to provide a power signal to the stimulator. This power signal may be used to charge a power supply of the stimulator and/or power operation of the device. For example, when the stimulator comprises a passive stimulator such as discussed above, the stimulator may be configured to deliver stimulation while it receives power from the controller. In variations in which the stimulator is programmable, the stimulation may be configured to deliver stimulation on a scheduled basis, and need only communicate with the controller intermittently for recharging a power source of the stimulator, reprogramming the stimulator, and/or retrieving data from the stimulator.

In some instances, it may be desirable for the stimulator to deliver periodic or repeated stimulation. Accordingly, the stimulator and/or controller may be configured such that the stimulator delivers stimulation at programmed intervals. In some such variations, the controller and/or stimulator may be programmed to deliver stimulation multiple times a day (e.g., two, three, four, or more times a day). In some variations, the stimulator and/or controller may be programmed to deliver stimulation multiple times a day according to a predetermined schedule. In variations where the stimulator is programmable, the stimulator may be programmed to deliver stimulation according to the predetermined schedule. In variations where the stimulator comprises a passive stimulation circuit, the controller may be programmed to deliver power to the stimulator (during which the stimulator may stimulate) at specific times according to the predetermined schedule. In other variations, the controller may be positioned in a location where the animal will typically be in proximity (e.g., sufficient proximity to allow the controller to communicate with the stimulator) to the controller multiple times during the day. For example, the controller may positioned in or on, a cage, animal bed, or food or water bowl, as described in more detail below. In these variations, the animal may generally move toward these locations one or more times per day, which may result in periodic or repeated stimulation.

While shown in FIG. 1 as comprising a power supply (122), the controller (104) need not have a power supply (122). In some variations, the controller (104) may be configured to connect to an external source of power, such as a wall socket. In variations where the controller comprises a power supply (122), the power supply may be any suitable power supply (e.g., one or more batteries or the like).

In some variations, the controller (104) may also comprise an input module (124), but need not. In variations where the controller (104) comprises an input module (124), the input module may provide one or more input signals to the controller subsystem (118). In some variations, the input module (124) may comprise one or more input mechanisms such as one or more buttons, levers, or sliders that may allow an animal caretaker, veterinarian, or owner to provide one or more inputs to the controller subsystem (118). For example, a caretaker, veterinarian, or owner of the animal may manipulate an input mechanism to direct the controller (104) to instruct or otherwise power the stimulator (102) to provide stimulation, or may alter one or more stimulation parameters. In other variations, the input module (124) may comprise one or more sensors which may be configured to provide one or more input signals to the controller subsystem (118). For example, in some variations the input module (124) may comprise one or motion or proximity sensors, and the input module (124) may be configured to alert the controller subsystem (118) when the motion sensor detects a threshold level of motion. In these variations, the controller (104) may be configured to transmit one or more signals to the stimulator (102) when the motion sensor detects a threshold level of motion. For example, the controller (104) may be configured to instruct the stimulator (102) to begin providing stimulation. In some instances (such as when the stimulator (102) is a passive stimulator), the controller (104) may be configured to provide power to the stimulator (102). In other variations, the input module (124) may comprise one or more pressure sensors, and the controller (104) may be configured to transmit one or more signals to the stimulator (102) (such as described above) when the pressure sensor detects a threshold pressure applied thereto.

In some instances, in order to allow for communication between the controller (104) and the stimulator (102), it may be necessary to position the communication subsystem (116) of the stimulator (102) in the vicinity of the communication subsystem (120) of the controller (104). Accordingly, in some variations, the controller (104) may be incorporated into a controller system, which may be configured to facilitate signal transmission between the controller and the stimulator. For example, in some variations, the controller system may comprise a hand-held housing that may house some or all of the components of the controller. In these variations, an owner, veterinarian, or caretaker of the animal may manually place the housing near the communication subsystem of the stimulator to allow for signal transfer between the controller and the stimulator.

In some instances, it may inconvenient to require a user to manually hold the controller relative to the implanted stimulator, as the animal may have a tendency to move relative to the user and the controller. Accordingly, in some variations, a controller system may be configured to attach the controller to the animal. For example, in some variations, the controller system comprises at least one housing configured to house some or all the components of the controller. In these variations, the housing may comprise one or more adhesive layers which may at least temporarily adhere the controller the animal. In other variations the housing may comprise one or more clips, straps, or other fasteners which may allow the controller to be clipped to an ear of the animal.

Figure 5:
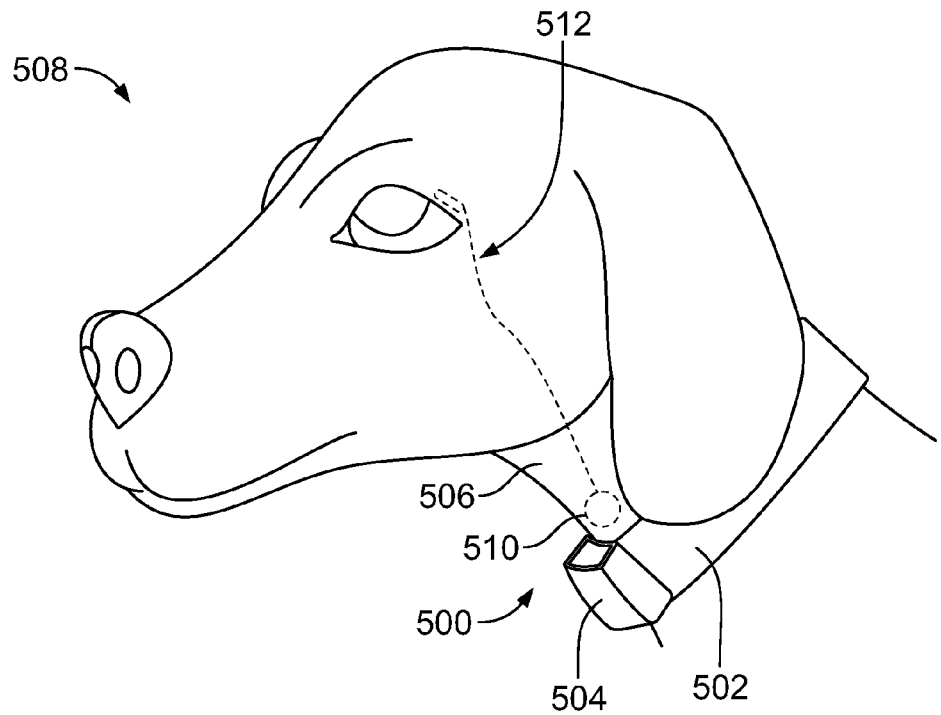
FIGS. 5 and 6 depict variations of controller system as described here each comprising a collar.

In other variations, the controller system may comprise a collar, bridle, or horse hood which may be used to connect the controller to the animal. In some of these variations, the controller system may comprise a collar, and the controller may be connected to the collar. For example, FIG. 5 depicts one variation of a controller system (500) comprising a collar (502) and a controller (504) attached thereto. The controller (504) may be permanently or releasably connected to the collar (502). When the controller (504) is releasably connected to the collar (502), the controller (504) may be connected to the collar using one or more clips, ties, magnets, or the like. When a communication subsystem of a stimulator is positioned in the neck of an animal, the collar (502) may be positioned around the neck of the animal (e.g., the neck (506) of a dog (508), as shown in FIG. 5), which may position a communication subsystem (not shown) of the controller (504) near the communication subsystem of a stimulator. For example, as shown in FIG. 5, a housing (510) of a stimulator (512) may be positioned in the neck (506), such that placing the collar (502) around the neck (506) of the dog (508) may place the controller (504) near the housing (510).

Figure 6:
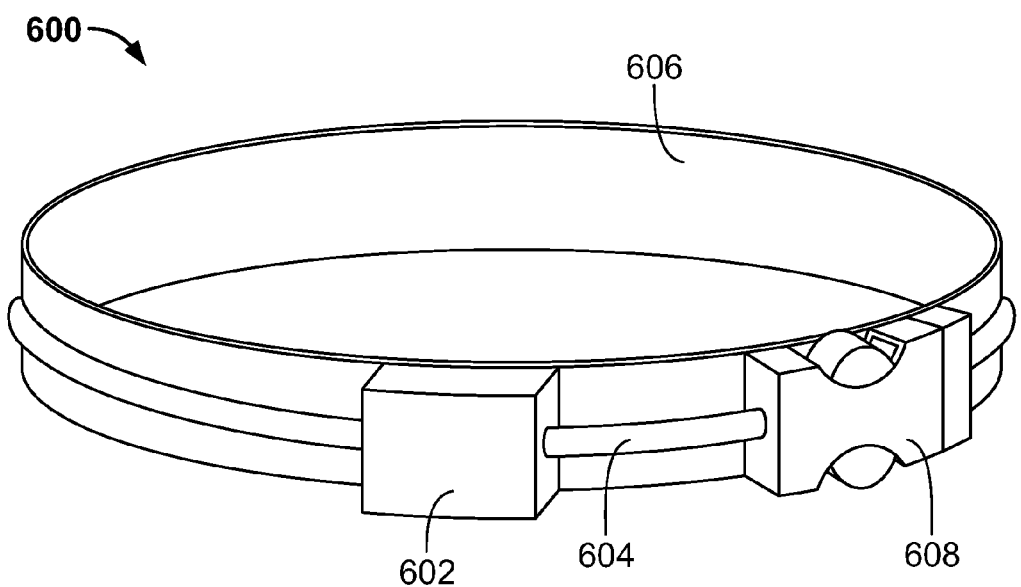

In some variations where the communication subsystem of a controller comprises a coil, the coil may be configured to encircle the head or neck of the animal. In these variations, signals generated by the coil may be directed toward the head of the animal, which may facilitate communication with the communication subsystem of a stimulator that is positioned in the head of the animal. For example, FIG. 6 depicts one variation of a controller system (600) comprising a controller (602) attached (releasably or permanently) to a collar (606). As shown there, the controller (602) may comprise a coil (604) which may be connected to the collar (606) such that the coil (604) may encircle the head or neck of an animal when the collar (606) is placed around the head or neck of the animal.

In some instances, the collar (606) may comprise a latch (608) which may be configured to connect and release two ends of the collar (606) (e.g., to connect the collar to or release the collar from the head or neck of an animal), as illustrated in FIG. 6. When a coil (604) is positioned around the circumference of the collar (606), such as shown in FIG. 6, it may be necessary to disconnect two ends of the coil (604) in order to release the ends of the collar (606). Accordingly, the latch (608) may be configured to connect and disconnect the two ends of each of the coil (604) at the collar (606). In these variations, the latch (608) may be unlatched to disconnect the collar (606) and the coil (604), which may facilitate placement of the collar (606) and coil (604) around the head or neck of the animal. Once placed around the head or neck of the animal, the latch (608) may be latched to hold the collar (606) and coil (604) in place relative to the animal. It should also be appreciated that a coil need not be disconnected when the latch (608) disconnects two ends of the collar (606). In some variations, the coil (604) may be longer than the collar (606), such that the collar (606) may be disconnected (e.g., via the latch (608)), the coil may be slipped over the animals head to place the coil around the head or neck of the animal, and the collar (606) may be latched around the head or neck of the animal.

Figure 7A:
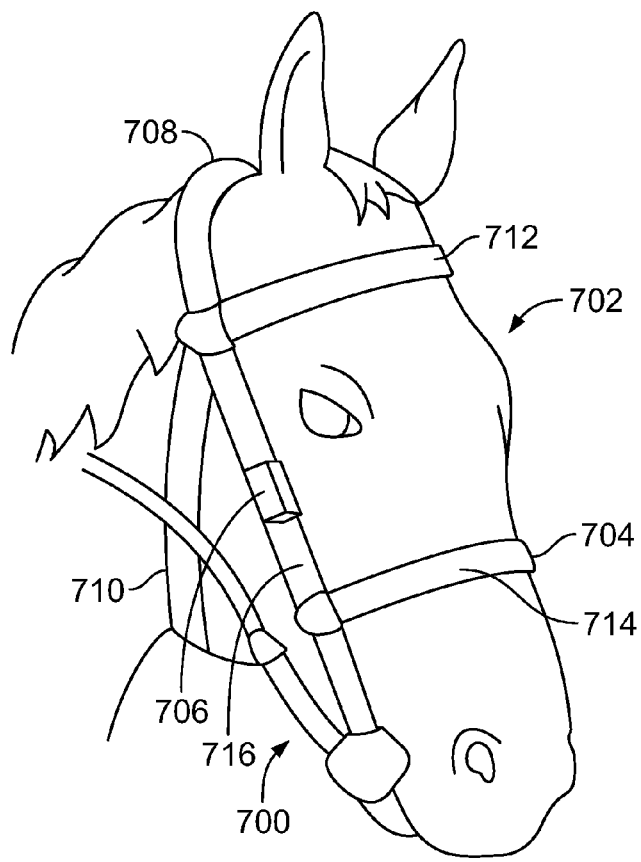
FIGS. 7A and 7B depict variations of the controller systems described here comprising a bridle.

In other variations, the controller system may comprise a bridle or a horse hood with a controller connected thereto. For example, FIG. 7A depicts a variation of a controller system (700) (depicted in FIG. 7A as being worn by a horse (702)) comprising a bridle (704) and a controller (706) to the bridle (704). As shown there, the bridle (704) may comprise a crownpiece (708), a throat lash (710), a browband (712), a nose band (714), and cheek straps (716). The controller (706) may be permanently or releasably attached to the bridle (704), and may be attached to any suitable portion of the bridle (704). For example, in some variations, at least a portion of the controller may be connected to a throat lash (710). In variations where a stimulator is implanted such that a communication subsystem of the stimulator is positioned near the neck or jaw of a horse (702), attaching the controller (706) (or a communication subsystem thereof) to the throat lash (710) may position a portion of the communication subsystem of the controller (706) near the communication subsystem of the stimulator. In some variations (as shown in FIG. 7A), at least a portion of the controller (706) may be connected to a cheek strap (716). These variations may find utility in instances where a stimulator is implanted such that a communication subsystem of the stimulator is positioned near the eye (e.g., adjacent to a lacrimal gland or a nictitans gland), as the controller system (700) may position a communication subsystem of the controller (706) near the communication subsystem of the stimulator. In still other variations, at least a portion of the controller (706) may be attached to the browband (712). In still other variations, at least a portion of the controller (706) may be attached to the nose band (714). In yet other variations, the controller (706) at least a portion of may be attached to the crownpiece (708). It should be appreciated that in some variations, different portions of the controller (706) may be attached to different portions of the bridle (704) (for example, a communication subsystem or components thereof may be attached to a cheek strap (716), while a power supply may be attached to the throat lash (710).

Figure 7B:
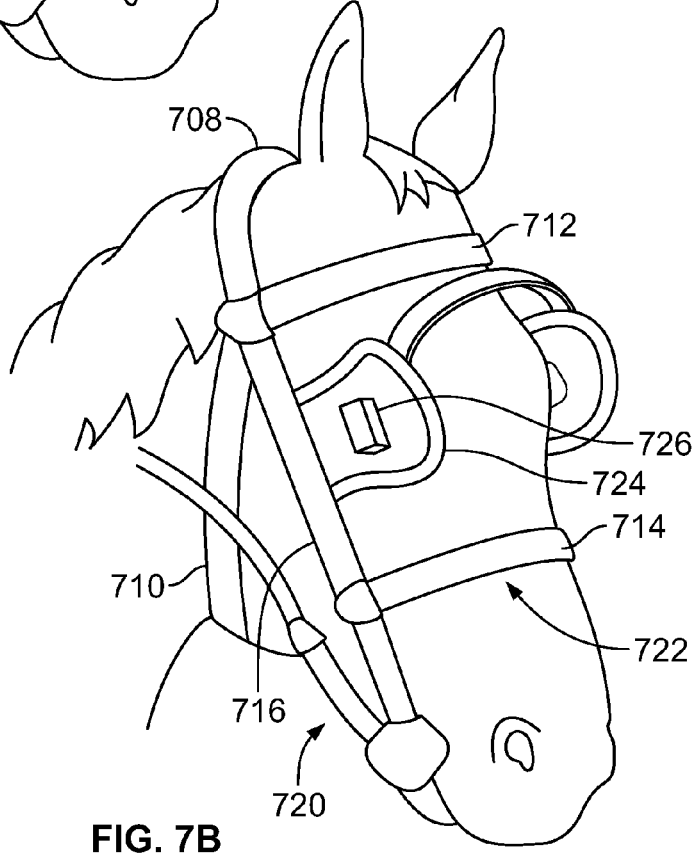

In some instances, the controller system may comprise a bridle or horse hood comprising blinders. In some of these variations, at least a portion of the controller may be attached to the blinders. For example, FIG. 7B shows a second variation of a controller system (720) comprising a bridle (722) having blinders (724) (components of the bridle (722) that are identical to those the bridle (704) shown in FIG. 7A are labeled the same as in FIG. 7A) and a controller (726). As shown there, at least a portion of the controller (726) may be attached to at least one of the blinders (724). In variations where a communication subsystem of a stimulator is positioned around the eye (e.g., adjacent the lacrimal and/or nictitans gland), positioning at least a portion of the controller (726) on a blinder may position a communication subsystem of the controller (726) near the communication subsystem of the stimulator.

Figure 8A:
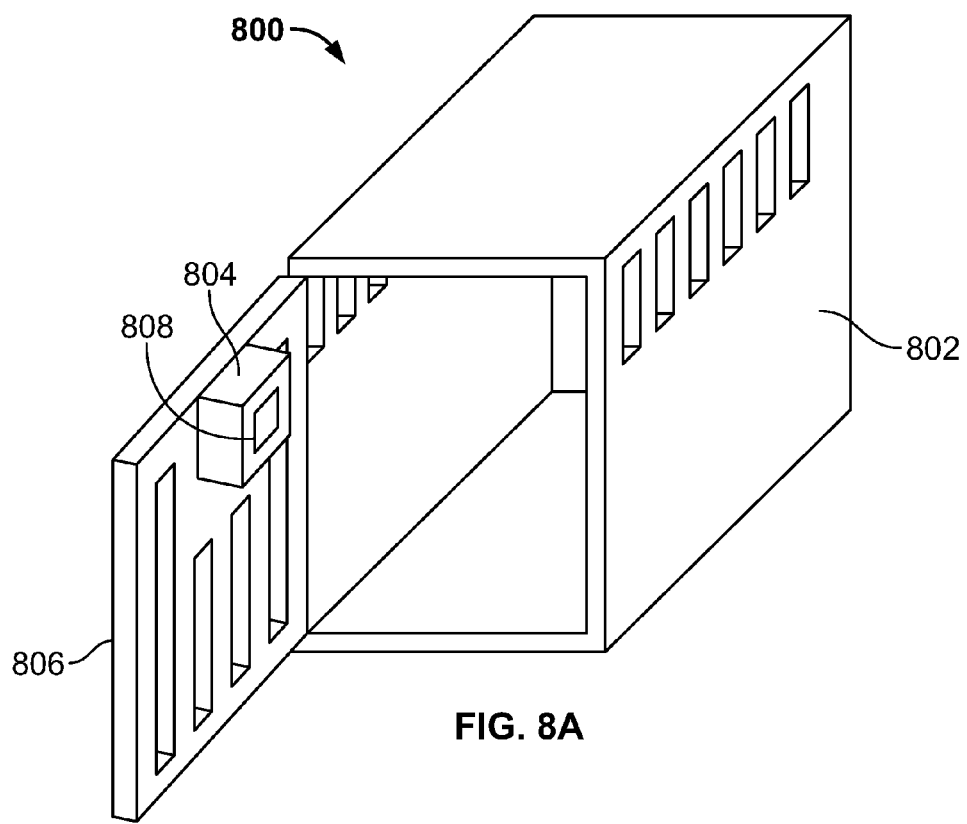
FIGS. 8A-8D depict variations of the controller systems described here comprising a cage.

In other variations, a controller system may comprise a crate/cage and a controller attached thereto. In these variations, the controller may be configured to transmit one or more signals to an implanted stimulator when the animal is in the cage. FIG. 8A depicts one variation of a controller system (800) comprising a cage (802) and a controller (804). The controller (804) may be releasably or permanently attached to the cage (802). The controller (804) may be attached to any suitable portion of the cage (e.g., a wall, floor, ceiling, or door thereof). For example, in the variation of the controller system (800) shown in FIG. 8A, the controller (804) may be attached to a door (806) of the cage (802).

When the controller system comprises a cage and a controller, the controller may comprise one or more sensors configured to detect when an animal is in or near the cage. In these variations, the controller may be configured to begin transmitting a signal to an implanted stimulator (e.g., via a communication subsystem of the controller) when the sensor detects the presence of the animal. In some variations, the controller may be configured to generate the signal for as long as the sensor detects the presence of the animal. In other variations, the controller may be configured to generate a signal for a predetermined interval each time the sensor detects the presence of the animal. The sensor may be any suitable sensor, such as a motion sensor, a pressure sensor, or the like. For example, in the variation of the controller system (800) shown in FIG. 8A, the controller (804) may comprise a motion sensor (808). In these variations, the controller (804) may comprise an input module (not shown), such as described above, which may be configured to alert a controller subsystem (not shown) of the controller (804) when the motion sensor (808) detects motion. Accordingly, the controller (804) may be configured to generate and transmit one or more signals when the motion sensor (808) detects motion. For example, when an animal with an implanted stimulator (such as described in more detail above) approaches and/or enters the cage (802), the motion sensor (808) may detect this movement, and the controller (804) may transmit power and/or data signals to the stimulator.

Figure 8B:
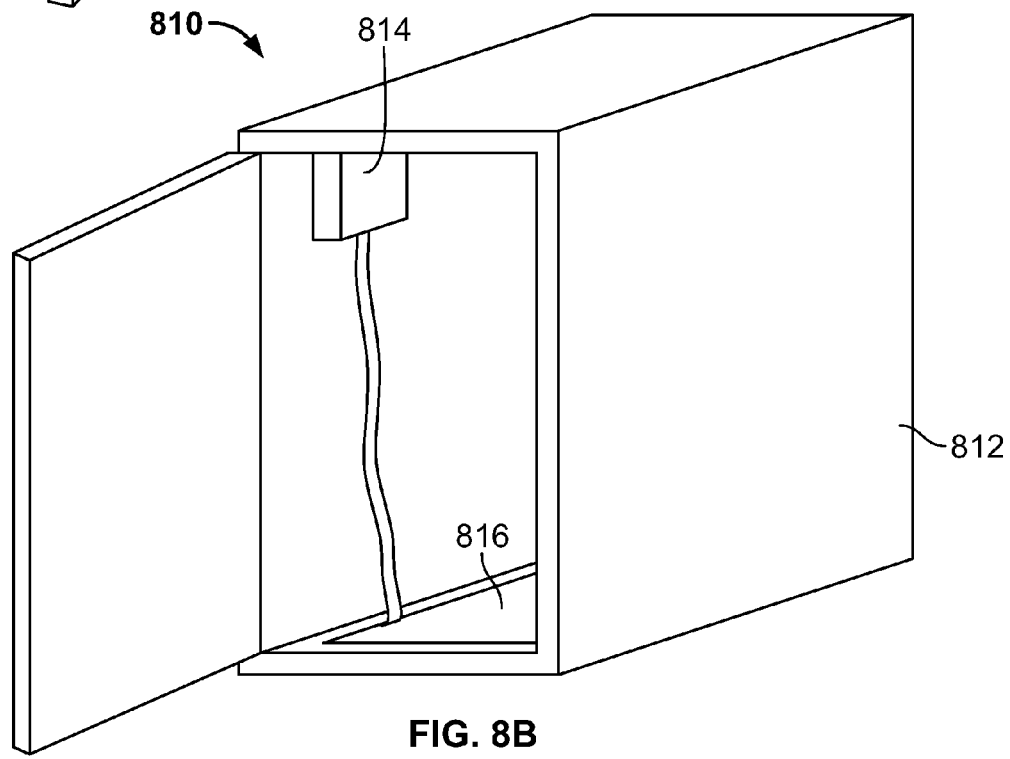

FIG. 8B shows another variation of another controller system (810) comprising a cage (812) and a controller (814). Again, the controller (814) may be releasably or permanently attached to the cage (812). In this variation, the controller may comprise one or more pressure sensors (816). The pressure sensor or sensors (816) may be configured to detect pressure applied thereto. Accordingly, the pressure sensors (816) may be attached or otherwise incorporated into the floor of the cage (812), and may determine the pressure that is applied to the floor of the cage (812). The controller (814) may be configured to generate and transmit one or more signals (e.g., power and/or data signals) to an implanted stimulator when the pressure monitored by the pressure sensors (816) reaches a threshold level. For example, when an animal stands, sits, or lays in the cage (812), the pressure sensors (816) may detect the weight of the animal, and the controller (814) may generate and transmit one or more signals to a stimulator implanted in the animal.

Figure 8C:
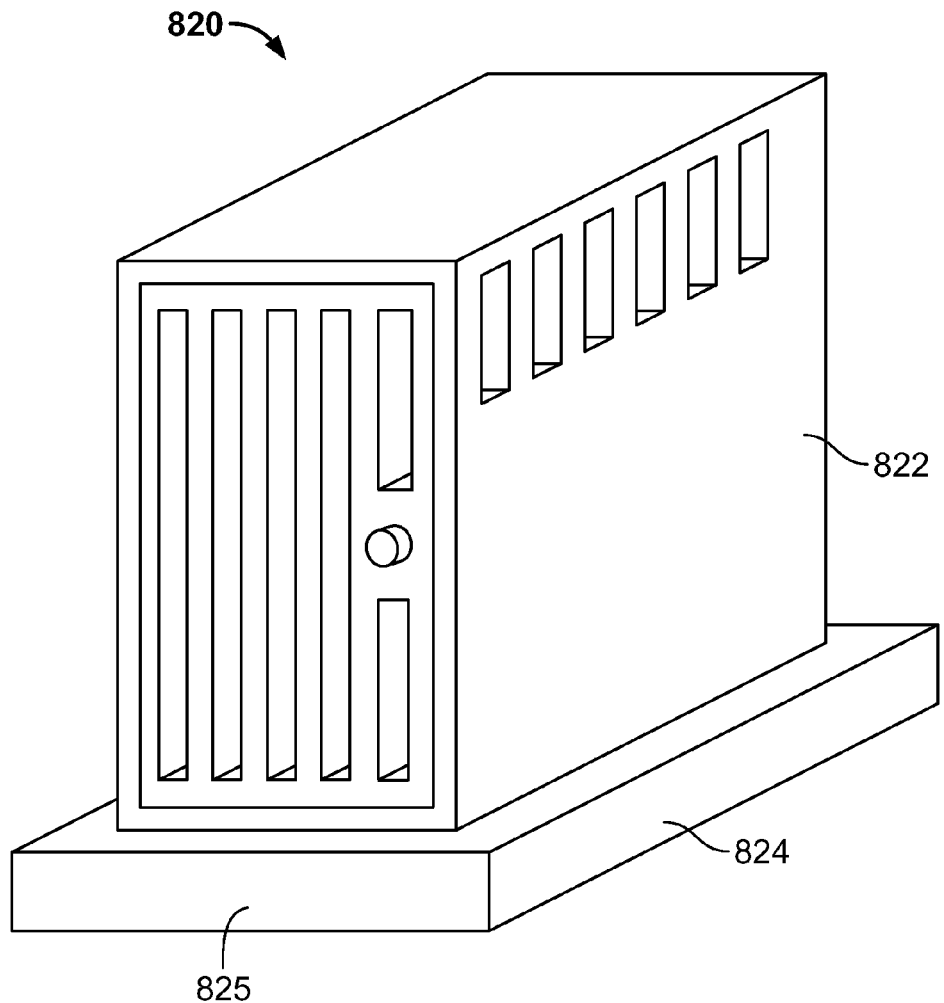
Figure 8D:
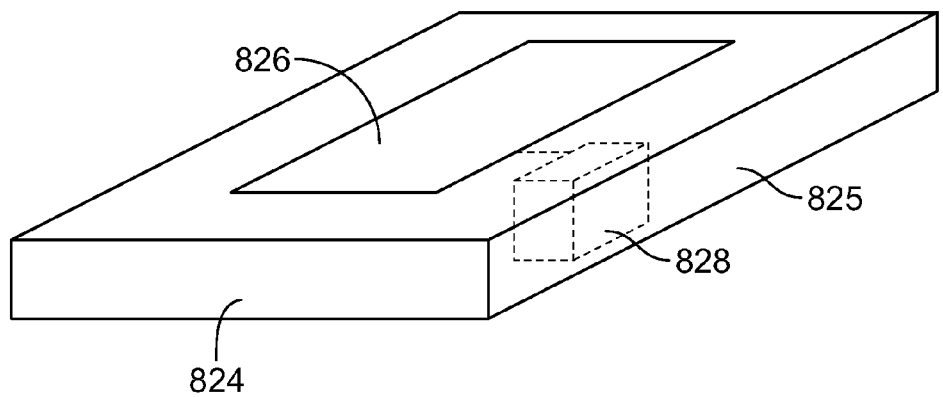

FIGS. 8C and 8D show a second variation of controller system (820) comprising a cage (822) and a controller (824). In these variations, the controller (824) may be configured as a platform (825) having an upper surface sized and configured to receive the cage (822). The cage (822) may be placed on the upper surface of the platform (825) (as shown in FIG. 8C), and in some instances may be fixed relative to the platform (825). In these variations, the cage (822) may be permanently fixed to the platform (825) (e.g., via bonding, welding, or the like) or may be releasably fixed to the platform (825) (e.g., via one or more latches, clips, lashes, or the like). In some variations, such as shown in FIG. 8D (with the cage (822) not illustrated), the controller (824) may comprise a pressure sensor (826) which may be positioned on or in the platform (825). When the cage (822) is positioned on an upper surface of the platform (825) (such as shown in FIG. 8C), the pressure sensor (826) may measure pressure applied thereto by the cage (822) and its contents. The pressure measured by the pressure sensor (826) may be monitored by other portions of the controller circuitry (depicted in FIG. 8D by element (828)), and the controller (824) may be configured to generate and transmit one or more signals when the pressure measured by the pressure sensor (826) reaches a threshold level. The controller (824) may be configured such that the threshold level is met when the cage (822) is placed on the platform (825) (e.g., the controller (824) may be configured to generate one or more signals when the cage (822) is placed on the platform), in other variations, the threshold level may be calibrated or otherwise altered to account for the weight of the cage (822) and may be set such that it is met when a target animal is present in the cage (822) (e.g., the controller (824) may generate the one or more signals when the animal is present in the cage (822). Additionally, while the controller circuitry (828) may be incorporated into the platform (825), it should be appreciated that in some instances that one or more portions of the controller circuitry may be housed separately from the platform (825).

In still other variations, a controller system comprising a cage and a controller may be configured to generate and transmit signals when a door of the cage is closed. In these variations, the controller system may be able to determine whether the door of the cage is opened or closed (e.g., using one or more sensors or the like). When the controller determines that the cage door is closed, the controller may generate and transmit one or more signals to a stimulator. Conversely, when the controller determines that the cage door is open, the controller may cease generating and transmitting the one or more signals. Accordingly, when an animal is placed in the cage and the door is closed to keep the animal in the cage, the controller may generate and transfer signals to one or more stimulators implanted in the animal, such as described above. In still other variations, the controller may be configured to generate the signals continuously, or intermittently on a scheduled basis.

Figure 9A:
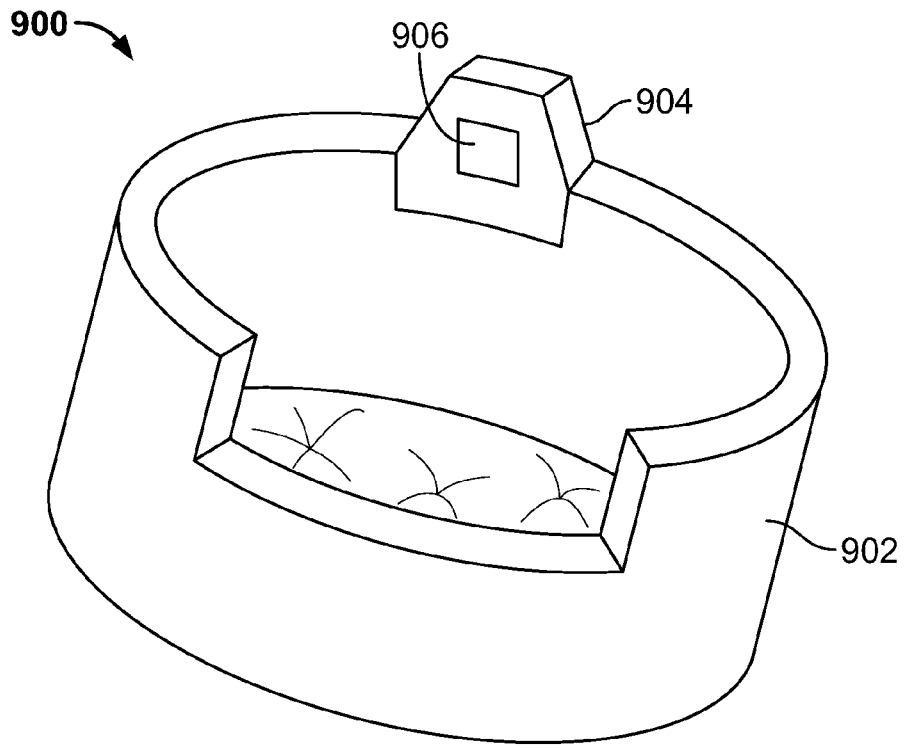
FIGS. 9A and 9B depict variations of the controller systems described here comprising an animal bed.
Figure 9B:
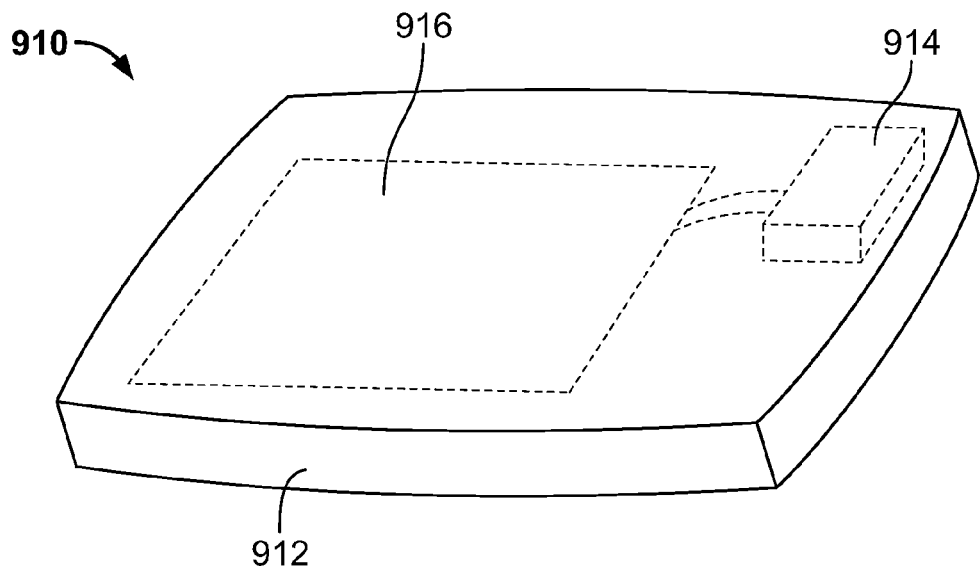

In other variations of the controller systems, the controller system may comprise an animal bed and a controller. For example, FIG. 9A shows a variation of a controller system (900) comprising an animal bed (902) and a controller (904) attached thereto. The controller (904) may be permanently or releasably attached to the animal bed (902). In some of these variations, the controller (904) may be at least partially housed within the animal bed (902). For example, FIG. 9B shows a second variation of a controller system (910) comprising an animal bed (912) and a controller (914) housed in the animal bed (902).

In some variations, a controller system comprising an animal bed may also have one or more sensors configured to detect the presence of an animal near or on the bed. In some variations, the controller system may comprise a motion sensor. For example, in the variation of the controller system (900) shown in FIG. 9A, the controller (904) may comprise a motion sensor (906). The motion sensor (906) may be configured to detect movement, and the controller (904) may be configured to generate and transmit one or more signals when the motion sensor (906) detects motion, such as described in more detail above. In other variations, the controller system may comprise one or more pressure sensors. In these variations, the pressure sensors may be configured to measure pressure applied to the bed. For example, in the variation of the controller system (910) shown in FIG. 9B, the controller (914) may comprise at least one pressure sensor (916) positioned on or in the bed (912). The at least one pressure sensor (916) may be configured to measure force applied to the bed (912) (e.g., by an animal standing or laying on the bed (912)), and the controller (914) may be configured to generate or transmit one or more signals when the force or forces measured by the at least one pressure sensor (916) reaches a threshold level. It should also be appreciated that in some instances the controller may be configured to continually transmit signals, or may be configured to transmit signals on a timed basis.

In still other variations of the controller systems described here, the controller system may comprise a controller and a food bowl (i.e., a bowl, trough, or other container configured to hold food and/or water). When the controller system comprises a food bowl, the controller may generate and transmit signals to an animal when the animal is near the food bowl. In these variations, the controller may be permanently or releasably attached to the food bowl. In some variations, the controller may be attached to the food bowl via a stand member configured to hold the food bowl.

Figure 10A:
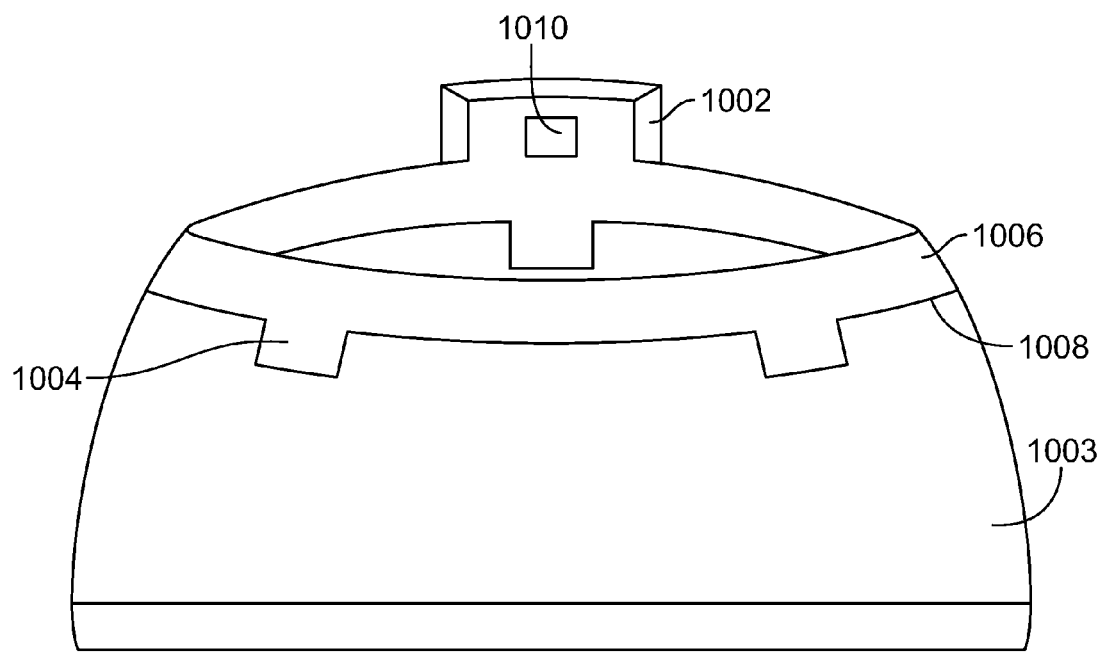
FIGS. 10A and 10B depict a variation of the controller systems described here comprising a food bowl.
Figure 10B:
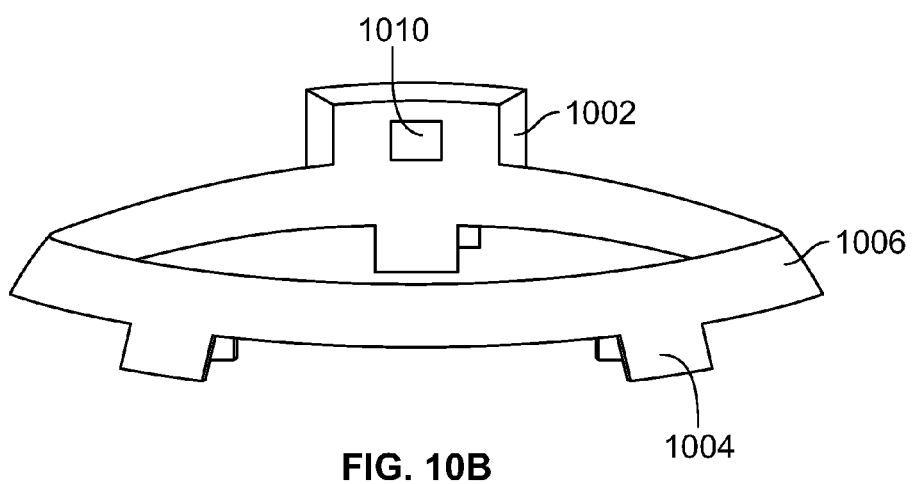

FIGS. 10A and 10B show one variation of a controller system (1000) comprising a controller (1002) and a food bowl (1003). As shown in FIG. 10A, the controller (1000) may be releasably connected to the food bowl (1003) via clips (1004). While clips (1004) are shown in FIG. 10A to connect the controller (1002) and the food bowl (1003), the controller (1000) may be connected to the food bowl (1003) by any suitable attachment mechanism (e.g., one or more magnets, adhesives, welding or bonding, etc.). FIG. 10B shows a perspective view of the controller (1002) without the food bowl (1003). As shown there, the controller (1002) may comprise a ring member (1006). The ring member (1006) may be sized and configured to sit or otherwise rest on a lip (1008) of the food bowl (1003) (as shown in FIG. 10A), or may be configured to at least partially encircle an outer wall of the food bowl (1003). In some variations where the controller (1002) comprises a communication subsystem (not shown) comprising a coil (not shown), the coil may be configured to be positioned around the circumference of the ring member (1006), which may in turn position the coil around the circumference of either the lip (1008) or outer wall of the food bowl (1003) when the controller (1002) is connected to the food bowl. Positioning a coil around the circumference of a lip or outer wall of a food bowl may facilitate transmission of a signal towards the head of an animal when the animal is eating or drinking from the food bowl.

In some variations, a controller system comprising a food bowl may also have one or more sensors configured to detect the presence of an animal near or on the bed. In some variations, the controller system may comprise a motion sensor. For example, in the variation of the controller system (1000) shown in FIGS. 10A and 10B, the controller (1002) may comprise a motion sensor (1010). The motion sensor (1010) may be configured to detect movement, and the controller (1002) may be configured to generate and transmit one or more signals when the motion sensor (1010) detects motion, such as described in more detail above. In other variations, the controller system may comprise one or more pressure sensors. In these variations, the pressure sensors may be configured to measure pressure applied to an area surrounding the food bowl. For example, in some variations the controller may comprise a pressure pad that may be placed under or near the food bowl. The controller may be configured to measure force or forces applied to the pressure pad (e.g., via one or more pressure sensors incorporated therein), and the controller may be configured to transmit one or more signals when the force or forces reaches a threshold level.

Generally, the systems described above may be used to treat one or more conditions in an animal. For example, in some instances, the systems described above may be used to treat dry eye in an animal. In some instances, the animal may be a horse. In other instances, the animal may be a dog. In yet other instances, the animal may be a cat. Generally, a stimulator may be implanted in the animal to position at least one electrode adjacent to a target tissue of the animal, and the stimulator may provide stimulation to the target tissue. In some variations, the target tissue may be a lacrimal gland, and at least one electrode of the stimulator may be placed adjacent to the lacrimal gland. In these variations, the stimulator may apply stimulation to the lacrimal gland, or one or more cells or nerves thereof. In other variations, the target tissue may be a nictitans gland, and at least one electrode of the stimulator may be placed adjacent to the nictitans gland. In these variations, the stimulator may apply stimulation to the nictitans gland, or one or more cells or nerves thereof. In still other variations, at least one first electrode may be positioned adjacent a lacrimal gland, and at least one second electrode may be positioned adjacent a nictitans gland, and stimulation may be applied to both the nictitans and the lacrimal gland. In some of these variations, the at least one first electrode and the at least one second electrode may connected to the same stimulator. In others of these variations, the at least one first electrode may be connected to a first stimulator implanted in the animal, and the at least one second electrode may be connected to a second stimulator implanted in the animal. In some instances, the stimulators may be implanted using one or of the procedures and devices described in U.S. patent application Ser. No. 13/441,806, filed on Apr. 6, 2012, which was previously incorporated by reference in its entirety.

In some instances, one or more controller systems may transmit one or more signals to the stimulator, such as described in more detail below. Any of the controller systems described above may be used to transmit the one or more signals to the stimulator. In some variations, the controller system may be configured to transmit one or more signals to the stimulator when a motion sensor of the controller system detects motion. In other variations, the controller system may be configured to transmit one or more signals to the stimulator when a pressure sensor of the controller system detects a threshold level of pressure. In some variations, the controller may receive one or more signals, such as a data signal, from the stimulator.

We claim:

1. A system for treating an animal comprising:
    an implantable stimulator configured for implantation in the animal; and
    a controller system comprising a controller, wherein the controller is configured to transmit one or more signals to the implantable stimulator,
    and wherein the controller system comprises a horse bridle or horse hood, and wherein the controller is connected to the horse bridle or horse hood.

2. The system of claim 1 wherein the horse bridle comprises a cheek strap and wherein at least a portion of the controller is connected to the cheek strap.

3. The system of claim 1 wherein the horse bridle comprises a throat lash and wherein at least a portion of the controller is connected to the throat lash.

4. The system of claim 1 wherein the horse bridle or horse hood comprises a blinder and wherein at least a portion of the controller is connected to the blinder.

5. A method of treating dry eye in an animal comprising:
   implanting a stimulator in the animal to position at least one electrode adjacent a lacrimal gland or a nictitans gland of the animal; and
   applying a stimulation signal to the lacrimal gland or the nictitans gland,
   wherein positioning at least one electrode adjacent the lacrimal gland or the nictitans gland comprises positioning a first electrode adjacent the lacrimal gland and positioning a second electrode adjacent the nictitans gland.

6. The method of claim 5 wherein applying a stimulation signal to the lacrimal gland or the nictitans gland comprises applying a first stimulation signal to the lacrimal gland and applying a second stimulation signal to the nictitans gland.

7. A method of treating dry eye in an animal comprising:
   implanting a stimulator in the animal to position at least one electrode adjacent a lacrimal gland or a nictitans gland of the animal;
   applying a stimulation signal to the lacrimal gland or the nictitans gland; and
   transmitting at least one signal from a controller of a controller system to the stimulator,
   wherein the controller system comprises a motion sensor, wherein transmitting the at least one signal from the controller to the stimulator comprises transmitting the at least one signal when the motion sensor detects a threshold level of motion.

* * * * *